United States Patent
Charlebois et al.

(10) Patent No.: US 8,123,876 B2
(45) Date of Patent: Feb. 28, 2012

(54) METHOD FOR BONDING COMPONENTS OF MEDICAL DEVICES

(75) Inventors: Steven J. Charlebois, West Lafayette, IN (US); W. Kurt Dierking, West Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 626 days.

(21) Appl. No.: 12/332,875

(22) Filed: Dec. 11, 2008

(65) Prior Publication Data
US 2009/0151819 A1   Jun. 18, 2009

Related U.S. Application Data

(60) Provisional application No. 61/013,553, filed on Dec. 13, 2007.

(51) Int. Cl.
*C22F 1/00* (2006.01)

(52) U.S. Cl. .......... 148/527; 148/563; 623/1.18

(58) Field of Classification Search .......... None
See application file for complete search history.

(56) References Cited

U.S. PATENT DOCUMENTS

| | | | |
|---|---|---|---|
| 3,579,805 A | 5/1971 | Kast | |
| 4,198,081 A | 4/1980 | Harrison et al. | |
| 4,631,796 A | 12/1986 | Inomata et al. | |
| 4,637,962 A * | 1/1987 | Albrecht et al. | 428/616 |
| 5,058,936 A | 10/1991 | Kapgan et al. | |
| 5,120,308 A * | 6/1992 | Hess | 604/170.01 |
| 5,358,796 A | 10/1994 | Nakamura et al. | |
| 5,485,667 A | 1/1996 | Kleshinski | |
| 5,540,712 A * | 7/1996 | Kleshinski et al. | 623/1.19 |
| 6,043,451 A | 3/2000 | Julien et al. | |
| 6,637,110 B2 | 10/2003 | Jee | |
| 7,111,645 B1 | 9/2006 | Fry | |
| 7,243,408 B2 | 7/2007 | Vietmeier | |
| 2002/0187020 A1 | 12/2002 | Julien | |
| 2005/0021046 A1 | 1/2005 | Bilge | |
| 2005/0196633 A1 * | 9/2005 | Doh et al. | 428/615 |
| 2005/0207896 A1 * | 9/2005 | Gigliotti et al. | 416/241 R |
| 2005/0240259 A1 | 10/2005 | Sisken et al. | |
| 2006/0047223 A1 * | 3/2006 | Grandfield et al. | 600/585 |
| 2007/0093888 A1 | 4/2007 | Thistle et al. | |

FOREIGN PATENT DOCUMENTS

WO   WO-2007/001392 A2 *   1/2007

* cited by examiner

*Primary Examiner* — George Wyszomierski
(74) *Attorney, Agent, or Firm* — Brinks Hofer Gilson & Lione

(57) ABSTRACT

A method of bonding a first component of a medical device to a second component of the medical device, where at least one of the components comprises a shape memory material, includes positioning the components in close proximity to each other to obtain an assembled configuration, and heating the assembled configuration at a temperature in the range of from about 800° C. to about 1100° C. to obtain a diffusion bond at a region of contact between the two components. The assembled configuration is formed into a desired set shape and heat-set at a temperature in the range of from about 350° C. to about 550° C. to impart a memory of the desired set shape to the shape memory materials without substantially impairing the diffusion bond.

17 Claims, 5 Drawing Sheets

FIG. 9A
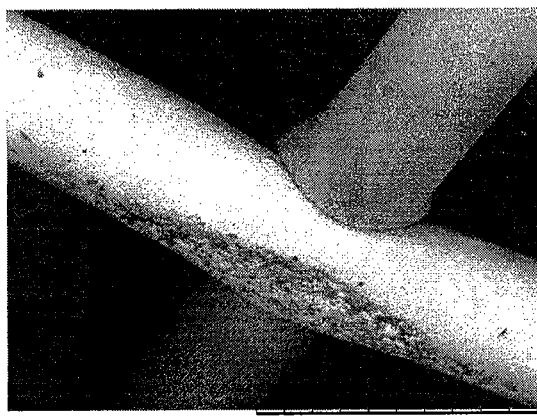
2008/11/26  16:23  x100  1 mm
NiTi/NiTi-Ta
FIG. 9B
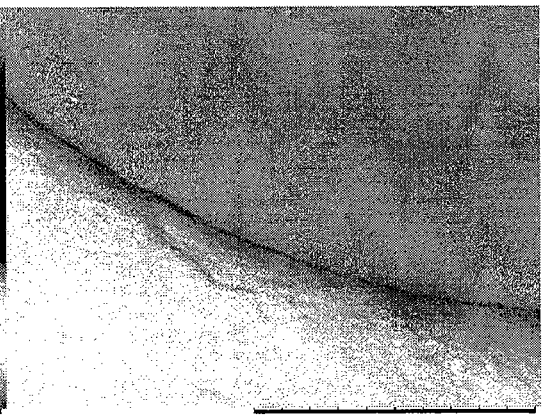
2008/11/26  16:26  x1.0k  100 um
NiTi/NiTi-Ta
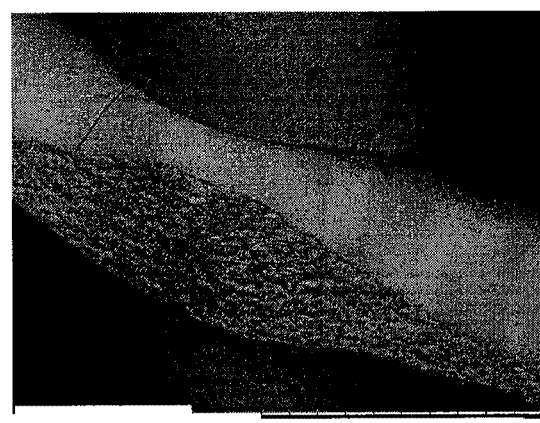
2008/11/26  15:52  x200  500 um
NiTi/NiTi
2008/11/26  15:36  x100  1 mm
NiTi/NiTi
FIG. 10A
FIG. 10B

METHOD FOR BONDING COMPONENTS OF MEDICAL DEVICES

RELATED APPLICATIONS

The present patent document claims the benefit of the filing date under 35 U.S.C. §119(e) of U.S. Provisional Patent Application Ser. No. 61/013,553, filed Dec. 13, 2007, which is hereby incorporated by reference in its entirety.

TECHNICAL FIELD

The present disclosure is related generally to medical device manufacturing, and more particularly to a bonding method for medical device components.

BACKGROUND

Prosthetic devices that are delivered intraluminally, such as stents, valves, occluders, shunts, etc., are typically designed to be self-expanding or balloon-expandable such that they engage the walls of the vessel or duct at the treatment site. To ensure that the prosthesis does not migrate after placement, anchoring barbs configured to embed into adjacent tissue may be employed to hold the device in place. Barbs are an especially important component of endovascular stent grafts, which are used to exclude an aneurysm sac formed in a blood vessel. The high velocity of blood within the aorta makes it essential to securely anchor the prosthesis when treating an aortic abdominal aneurysm (AAA). Migration of the device downstream can result in the proximal seal of the aneursym sac being compromised, which could be catastrophic in the event that the aneurysm sac ruptures. Barb fixation is thus employed in a variety of intraluminal prostheses, such as the ZENITH® Endovascular Stent Graft (Cook Incorporated), which relies on barbs to anchor the proximal end of the device in the healthy portion of the aorta above the renal arteries.

In an intraluminal prosthesis formed from a wire frame or support structure, the barbs typically comprise separate elements attached to the frame at strategic points therealong. Typically, short sections of material are soldered to struts of the frame such that they extend outward for engaging tissue. In the body, solder is subject to corrosion when in contact with bodily fluids, and therefore mechanical methods of attachment have been used as an additional measure to reduce the incidence of barb failure. However, in environments in which there are repetitive mechanical stresses, barb failure due to fracture of the strut or weld remains a relatively common phenomenon. Such failures may be attributed in part to limitations of the barb design and the method of manufacture and/or attachment.

Laser welding is another technique commonly employed for attaching barbs to struts of an intraluminal prosthesis. Due to the localized heating of this process, however, a heat-affected zone having a nonuniform microstructure may be formed at the site of the weld. The heat-affected zone may include coarse grains, undesirable precipitates, and/or increased levels of impurities that can cause embrittlement of the microstructure, thereby increasing the likelihood of barb failure.

Accordingly, an improved attachment method that can reliably bond a barb to a strut of an intraluminal prosthesis is desired.

BRIEF SUMMARY

A method of bonding one component of a medical device to another component of the medical device that may provide advantages over previous attachment methods is described herein. The bonding method allows for the fabrication of a bonded assembly having superelastic properties. Preferably, one or both components of the medical device are formed in whole or in part of a shape memory material.

According to one aspect, the method comprises positioning a first component in close proximity to a second component to form an assembled configuration of the components. Preferably, at least one of the first and second components comprises a shape memory material. The assembled configuration is heat treated at a temperature in the range of from about 800° C. to about 1100° C. to obtain a bond between the first component and the second component at a region of contact therebetween. The assembled configuration is then formed into a desired set shape and heat-set at a temperature in the range of from about 350° C. to about 550° C. Accordingly, a memory of the desired set shape is imparted to the shape memory material without substantially impairing the bond between the first and second components.

According to another aspect, the method comprises positioning an anchoring element in close proximity to a portion of a stent to form an assembled configuration thereof. Preferably, at least one of the anchoring element and the portion comprises a shape memory material. The assembled configuration is heat treated at a temperature in the range of from about 800° C. to about 1100° C. to obtain a bond between the anchoring element and the portion at a region of contact therebetween. The assembled configuration is formed into a desired set shape and heat-set at a temperature in the range of from about 350° C. to about 550° C. Accordingly, a memory of the desired set shape is imparted to the shape memory material without substantially impairing the bond between the anchoring element and the portion of the stent.

According to another aspect, the method comprises positioning a first end of a wire in close proximity to a second end of the wire to form an assembled configuration thereof. Preferably, the wire comprises a shape memory material. The assembled configuration is heat treated at a temperature in the range of from about 800° C. to about 1100° C. to obtain a bond between the first and second ends of the wire at a region of contact therebetween. The assembled configuration is formed into a desired set shape and heat-set at a temperature in the range of from about 350° C. to about 550° C. Accordingly, a memory of the desired set shape is imparted to the shape memory materials without substantially impairing the bond between the first and second ends of the wire.

BRIEF DESCRIPTION OF THE DRAWINGS

FIGS. 9A and 9B are SEM images of a first exemplary nickel-titanium wire bonded to a second exemplary nickel-titanium wire, where the second exemplary Ni—Ti wire includes a tantalum coating to facilitate bonding; and FIGS. 10A and 10B are SEM images of a third exemplary nickel-titanium wire bonded to a fourth exemplary nickel-titanium wire.

DETAILED DESCRIPTION

Figure 1:
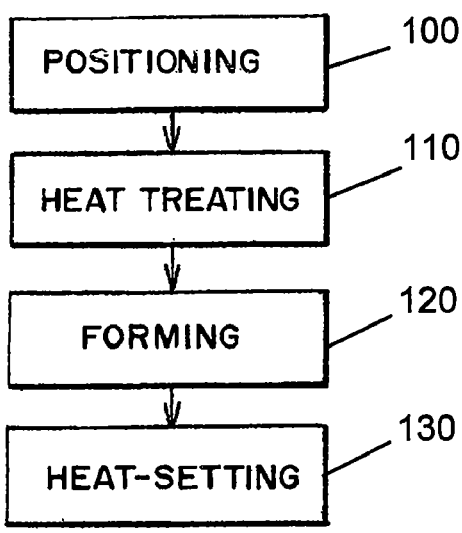
FIG. 1 is a flow chart showing steps of the method according to one aspect.
Figure 2A:
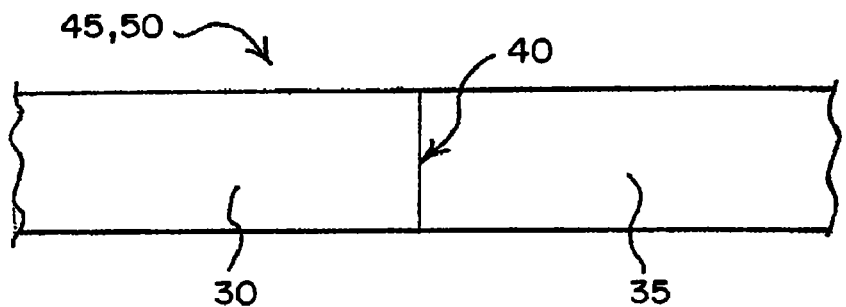
FIG. 2A is a schematic showing a first component of a medical device bonded to a second component of the medical device at a region of contact therebetween.
Figure 2B:
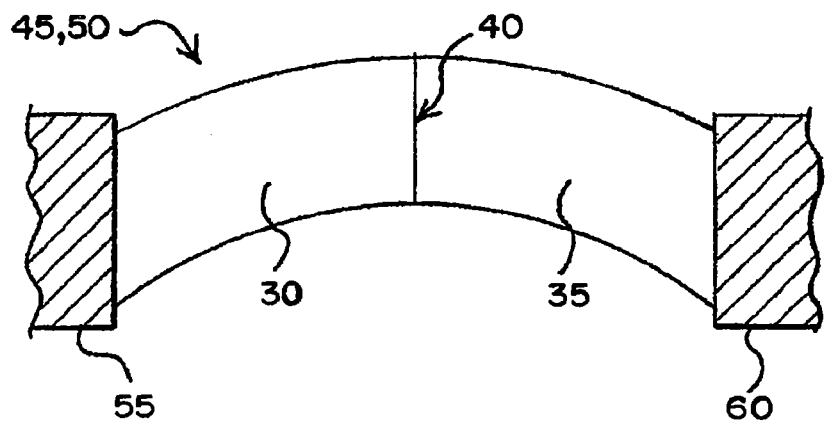
FIG. 2B is a schematic showing the bonded first and second components constrained into a final set shape for heat setting.

FIG. 1 is a flow chart showing steps of the bonding method according to one aspect. A first component 30 of the medical device 45 is positioned 100 in close proximity to a second component 35 of the medical device 45 to form an assembled configuration 50, as shown schematically in FIG. 2A. At least one of the first and second components 30, 35 is formed in whole or in part of a shape memory material. The assembled configuration 50 is then heat treated 110 at a temperature in the range of from about 800° C. to about 1100° C. to obtain a bond between the first component 30 and the second component 35 at a region of contact 40 therebetween. After being heat treated, the assembled configuration 50 is formed 120 into a final set shape. Heat-setting 130 is then carried out at a temperature in the range of from about 350° C. to about 550° C. The assembled configuration 50 may be constrained in the final set shape by one or more fixtures 55, 60 or other constraining members, as shown schematically in FIG. 2B, during the heat-setting. Thus, a "memory" of the final set shape may be imparted to the shape memory materials of the first and second components 30, 35 without substantially impairing the bond formed therebetween.

It is noted that the first and second components 30, 35 are positioned in sufficiently close proximity to each other for bonding if, during heat treating, there is a region of contact 40 between the components. The region of contact 40 may or may not be present prior to the heat treating step. Although the first and second components 30, 35 may be any medical device elements that are assembled together and bonded as described herein at a region of contact therebetween, the following exemplary description of the bonding method will focus on an anchoring element as the first component and a portion of an intraluminal medical prosthesis as the second component.

Figure 3:
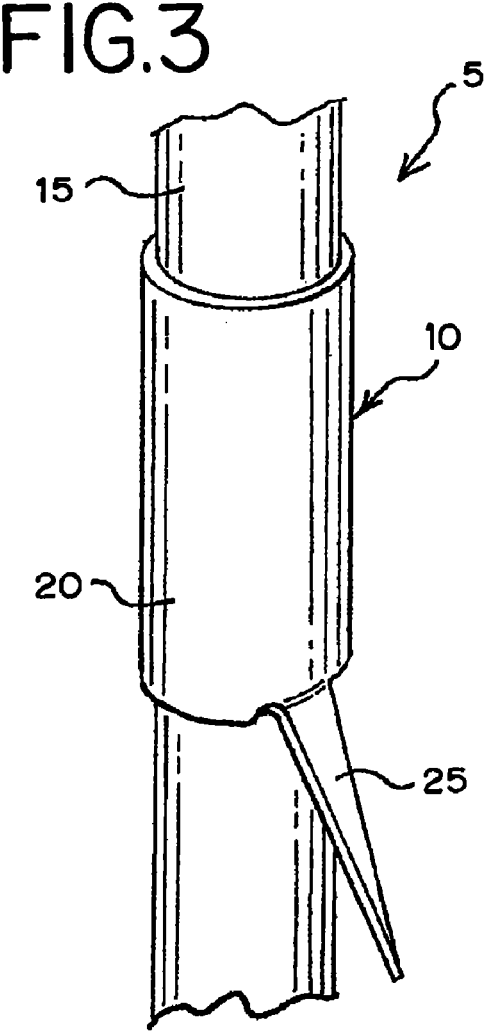
FIG. 3 is a perspective view of an anchoring element and a strut portion of a stent in an assembled configuration according to a first embodiment.
Figure 4:
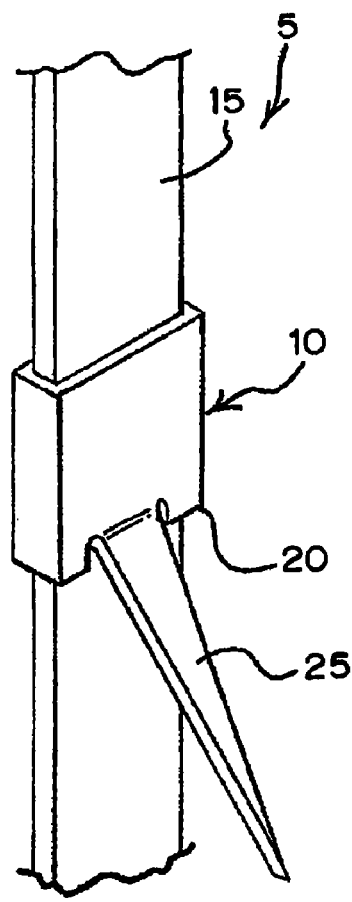
FIG. 4 is a perspective view of an anchoring element and a strut portion of a stent in an assembled configuration according to a second embodiment.

Referring to FIG. 3 or FIG. 4, the second component may be a strut portion 15 of a stent. The term "strut portion" refers to a part of the structure of a stent and includes, for example, both round wire segments, as shown in FIG. 3, and flat wire or cannula-cut strut segments, as shown in FIG. 4. The anchoring element 10 preferably includes an attachment portion 20 configured to at least partially surround the strut portion 15. An active fixation component (e.g., barb 25) adapted to penetrate tissue and provide mechanical fixation when deployed at a treatment site in a body vessel, extends from the attachment portion 20 of the anchoring element 10. The attachment portion 20 may comprise, for example, a thin-walled sleeve.

According to one aspect of the method, positioning 100 the attachment portion 20 of the anchoring element 10 and the strut portion 15 of the stent in close proximity to each other entails achieving a press-fit (or friction fit) between the two components in the assembled configuration. To obtain the press-fit, it is preferred that the attachment portion of the anchoring element has an inner dimension that is only fractionally larger (e.g., about 0.0005 inch (0.0013 cm) larger) than an outer dimension of the strut portion. The desired dimensions of the components may be obtained by machining, or by exploiting the shape memory properties of one or both components, as will be discussed further below. Obtaining a press-fit between the anchoring element 10 and the strut portion 15 prior to bonding may facilitate achieving a substantial region of contact (or interface) between the components during the heat treatment 110 step.

It may also be advantageous for the anchoring element 10 and the strut portion 15 to have complementary or mating surfaces to facilitate achieving the substantial region of contact. Thus, the specific geometry of the attachment portion 20 of the anchoring element 10 may be determined by the geometry of the strut portion 15. For example, if the strut portion 15 comprises a round wire, then the attachment portion 20 of the anchoring element 10 may be formed from a portion of a cannula (i.e., a thin-walled tube) or from a thin sheet of material curved to form a closed or partially open tubular configuration that at least partially surrounds the strut portion 15, as shown in FIG. 3. According to this example, the inner diameter of the anchoring element 10 is preferably fractionally larger than the outer diameter of the strut portion 15. In another example, if the strut portion 15 is formed from a flat wire or is laser-cut from a thin-walled cannula, then the attachment portion 20 of the anchoring element 10 may take the form of a thin-walled, generally rectangular structure which is sized to fit over the strut portion 15, as shown in FIG. 4. Other embodiments of the anchoring element 10 are illustrated in pending U.S. Patent Application No. 2005/02400259, filed on Jan. 27, 2005, which is hereby incorporated by reference in its entirety.

According to one aspect, the region of contact between the two components includes substantially all of the interior surface of the attachment portion 20 of the anchoring element 10 and substantially all of the exterior surface of the strut portion 15 facing the interior surface. According to another aspect, the region of contact may include only a portion of the interior surface of the attachment portion 20 and/or only a portion of the exterior surface of the strut portion 15.

To effect bonding, the assembled configuration is heat treated 110 at a temperature sufficient to promote the diffusion of atoms across the interface (i.e., the region of contact) between the attachment portion 20 and the strut portion 15, such that a diffusion bond may be formed therebetween. Preferably, the diffusion bond will join the components with an interface strength equal to or greater than the strength of the component materials. FIGS. 6A to 6D schematically illustrate the changes that occur at the interface during an exemplary bonding process.

Typically, the diffusion bonding temperature is about 60% of the melting temperature of the more fusible metal of the component materials. It is preferred that the heat treatment temperature is less than the melting point of the component materials so that the diffusion occurs in the solid state. Nitinol alloys, for example, have a melting temperature of about 1300° C. According to one aspect of the method, the heat treatment temperature lies in the range of from about 800° C. to about 1100° C. More preferably, the assembled configuration is heat treated at a temperature in the range of about 900° C. to about 1000° C.

In addition to the heat treatment temperature, the duration of the heat treatment and the pressure at the interface may affect the rate and extent of diffusion and, consequently, bond formation and strength. According to one aspect of the method, the duration (or "soak time") of the heat treatment may be in the range of from about 5 minutes to about 1.5 hours. Preferably, the soak time is in the range of from about 15 minutes to about 1 hour, or from about 30 minutes to about 1 hour.

The formation of the bond may be enhanced by the application of pressure to the interface between the anchoring element and the strut portion of the stent. Preferably, the pressure applied at the heat treatment temperature is sufficient to deform asperities and fill voids at the interface, and also to break-up any oxide films present on the surface of either component.

The applied pressure may be generated externally by, for example, one or more fixtures or clamps configured to hold the components in close contact with each other as the heat treatment is carried out. Carbon (e.g., graphite) thread may also be used as a means of constraining the components during the heat treatment. It is envisioned that the applied pressure may be generated internally by, for example, thermal expansion or shape recovery of at least one of the components in response to elevated temperatures, such as those provided during the heat treatment, as is discussed further below. According to one aspect of the method, the average pressure applied at the interface ranges from about 50 psi to about 500 psi, although other values are possible.

As noted above, the pressure applied to the interface between the anchoring element and the strut portion of the stent may be generated internally by a change in shape or dimension of one or both of the components. This change in pressure may be activated by an increase in temperature. For example, the assembled configuration of the anchoring element and the strut portion may be supported within a fixture having a coefficient of thermal expansion that is lower than the coefficient of thermal expansion of either of the component materials. Accordingly, during the heat treatment, thermal expansion of the anchoring element may generate an inward radial force that causes an increase in pressure at the interface between the anchoring element and the strut portion.

According to another embodiment, an internal pressure may be generated at the interface between the anchoring element and the strut portion due to shape recovery of one or both of the components during heating. According to this aspect of the method, one or both of the anchoring element and the strut portion of the stent may be formed in whole or in part from a shape memory alloy, such as Nitinol, which can "remember" and recover a previous shape. In the case of nickel-titanium shape memory alloys, the source of the shape recovery is a phase transformation between a lower temperature phase (martensite) and a higher temperature phase (austenite), which may be driven by a change in temperature (shape memory effect) or by the removal of an applied stress (superelastic effect). Strain introduced into the alloy in the martensitic phase to achieve a shape change may be substantially recovered upon completion of a reverse phase transformation to austenite, allowing the alloy to return to the previous shape. Austenite is characteristically the stronger phase, and martensite is the more readily deformable phase which may accommodate recoverable strains of up to about 8-10%.

As used herein, and as generally understood by one of skill in the art, martensite start temperature ($M_s$) is the temperature at which a phase transformation to martensite begins upon cooling for a shape memory material exhibiting a martensitic phase transformation. Martensite finish temperature ($M_f$) is the temperature at which the phase transformation to martensite concludes upon cooling. Austenite start temperature ($A_s$) is the temperature at which a phase transformation to austenite begins upon heating for a shape memory material exhibiting an austenitic phase transformation, and austenite finish temperature ($A_f$) is the temperature at which the phase transformation to austenite concludes upon heating.

Figure 5:
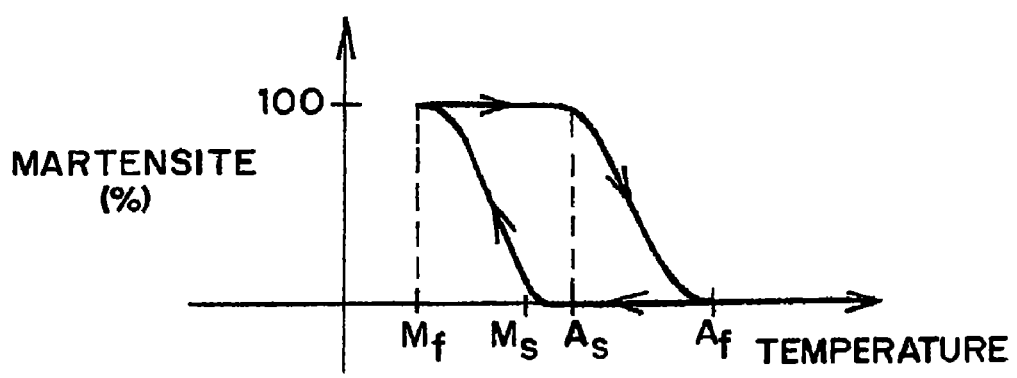
FIG. 5 shows a typical transformation temperature curve for an exemplary nickel-titanium shape memory alloy.
Figure 6A:
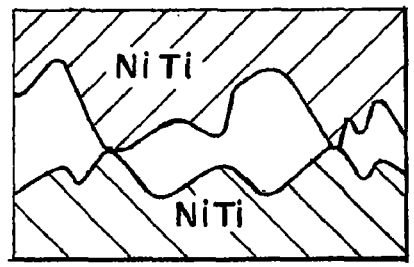
FIGS. 6A-6D show schematically the changes that occur at the interface between two components during an exemplary bonding process.
Figure 6B:
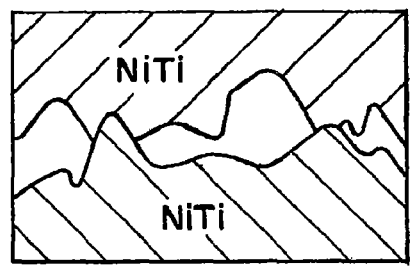
Figure 6C:
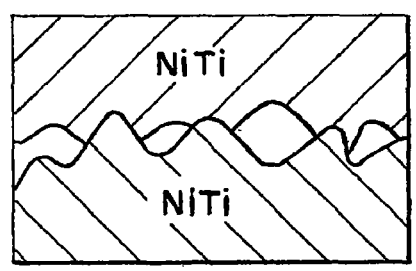
Figure 6D:
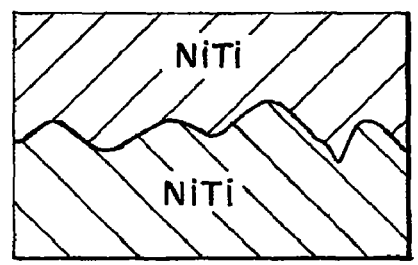

FIG. 5 shows a typical transformation temperature curve for an exemplary nickel-titanium shape memory alloy, where the y-axis represents the amount of martensite in the alloy and the x-axis represents temperature. At or above a temperature of $A_f$, the nickel-titanium alloy has a fully austenitic structure and an initial configuration. Following the arrows, the alloy may be cooled to a temperature of $M_s$, at which point the transformation to the martensitic phase begins. Further cooling leads to an increase in the percentage of martensite in the material, ultimately leading to a fully martensitic structure at a temperature of $M_f$. In the martensitic state, the alloy may be deformed to and retain another desired configuration. Upon heating to a temperature above $A_f$, the alloy transforms back to austenite and substantially recovers the initial configuration.

According to one aspect, both the anchoring element and the strut portion of the stent are formed of a nickel-titanium shape memory alloy. When assembled, the shape memory alloy of each component is preferably in the martensitic state. Upon warming the assembled configuration above the austenite finish temperature of the shape memory alloys, the anchoring element and the strut portion recover a previous configuration. Preferably, as a consequence of the phase transformation from martensite to austenite during the warming, the anchoring element radially shrinks an amount sufficient to exert an inward radial force on the outer surface of the strut portion, and the strut portion radially expands an amount sufficient to exert an outward radial force on the inner surface of the anchoring element, thereby generating a pressure at the interface between the two surfaces or the press-fit described above. It is also envisioned that only one of the two components may be formed of a nickel-titanium shape memory alloy; in this case, upon warming the assembled configuration above the austenite finish temperature ($A_f$) of the alloy, the component comprising the shape memory alloy expands, shrinks or otherwise changes dimension an amount sufficient to engage and press against the facing surface of the other component. Advantageously, a separate heating step may not be required, as the warming may be carried out as the temperature of the assembled configuration is raised to the desired heat treatment temperature for bonding.

Generally speaking, different combinations of heat treatment temperature, pressure, and soak time may be employed to obtain a diffusion bond between the anchoring element and the strut portion. For example, at higher heat treatment temperatures, it may be possible to form a reliable bond using shorter soak times and/or lower pressures.

Preferably, the heat treatment is carried out in a controlled environment to minimize contamination effects (e.g., oxidation) that may inhibit bond formation. A vacuum furnace in which a pressure of about $10^{-3}$ Torr to about $10^{-5}$ Torr or better is maintained, for example, may be suitable for the bonding process. A partial vacuum environment established by first evacuating the vacuum furnace and then backfilling with a low pressure of an inert gas such as argon or helium (e.g. less than about $10^{-2}$ Torr) may also be suitable for bonding.

Because of the sensitivity of shape memory materials to processing temperatures, the heat treatment performed to effect bonding may have an additional effect of altering the superelastic/shape memory properties of the bonded components. Accordingly, after the heat treatment has been completed and the diffusion bond formed, a heat-setting treatment (or anneal) may be carried out as a means of imparting (or resetting) the desired superelastic characteristics and a desired set shape of the bonded components.

Prior to heat-setting, the assembled configuration is formed into the desired set shape. It may be advantageous, prior to forming, to cool the assembled configuration to a temperature below $M_f$ to obtain a martensitic (and more deformable) microstructure of the assembled configuration. Once formed into the desired set shape, the components may be constrained by one or more fixtures, mandrels or other suitable constraining members to hold the set shape during the heat-setting treatment, which entails heating the assembled configuration to an appropriate temperature below the bonding temperature. Preferably, the heat-setting treatment is carried out at a temperature in the range of from about 350° C. to about 550° C. The heat setting treatment may be carried out for a duration of from about 10 minutes to about 30 minutes, according to one aspect, or from about 15 minutes to about 30 minutes.

The desired set shape may be a deployed configuration of the medical device. For example, it may be desirable for the barb to attain (i.e., to remember and recover) a configuration in which it extends away from the anchoring element at a predetermined angle to facilitate tissue penetration. Accordingly, during the heat-setting treatment, the barb may be constrained at the predetermined angle to impart a memory of this configuration. Similarly, the struts of the stent may be constrained in a radially expanded state during the heat-setting treatment to impart a memory of a configuration in which the stent has an expanded diameter to support a body vessel. Any mechanical or other method for fixturing or clamping the components in the desired shape may be employed for the constraining step.

During delivery of the medical device to a treatment site in a body vessel, the components are generally maintained in a low-profile delivery configuration. Once at the treatment site, the components may be deployed superelastically (e.g., by retraction of a tubular restraining sheath overlying the medical device) to the "remembered" higher profile deployed configuration.

The bonding method is believed to be particularly advantageous for bonding together components comprising shape memory alloys, such as equiatomic or near-equiatomic nickel-titanium alloys, including binary Ni—Ti alloys and also ternary and higher-order Ni—Ti alloys that contain additional alloying elements. Nickel-rich Ni—Ti alloys may be particularly suitable for bonding, and it may also be advantageous to use fully cold worked Ni—Ti alloys. For example, Ni—Ti alloys including at least about 30% cold work, or at least about 40% cold work, are believed to be suitable for the bonding method. Preferably, the Ni—Ti alloy includes at least about 50% cold work. The percentage of cold work refers to the amount of plastic strain imparted to the alloy during deformation (working). It is also preferred that the Ni—Ti alloys do not undergo a final anneal after working so as to retain the cold worked microstructure for bonding.

Other suitable shape memory alloys may include copper alloys, such as Cu—Zn—Al, Cu—Al—Ni, Cu—Zn—Sn, Cu—Sn, or Cu—Au—Zn; iron alloys, such as Fe—Mn, Fe—Mn—Si, Fe—Be, Fe—Pd or Fe—Pt; and other alloys, such as Ag—Cd, Au—Cd or In—Ti. The method may also be employed to bond together components comprising other metals or alloys. For example, one or both components may comprise stainless steel, titanium alloys (e.g., Ti-4Al-6V), precious metals (e.g., gold, platinum, or palladium), refractory metals (e.g., tantalum, tungsten, or molybdenum), or other materials. In one example, one or both components may be shape memory alloys that include a coating of tantalum or another metal or alloy, such as niobium. The presence of such a metal or alloy coating on one or both components may enhance the diffusion bonding process and lead to a stronger bond between the two components. The materials of the components are preferably biocompatible and capable of being diffusion bonded within a specified temperature range. According to one aspect, as described previously, the heat treatment temperature used for diffusion bonding is in the range of from about 800° C. to about 1100° C.

As described above, the first component employed in the bonding method may be an anchoring element that includes an active fixation component such as a barb adapted to penetrate tissue, and the second component may be a portion of an intraluminal medical prosthesis, such as a strut portion of a stent. The stent may be a self-expanding stent, a balloon expandable stent, a covered stent, or stent-graft. In addition, the bonding method is broadly applicable to other types of implantable or insertable medical devices having at least two components, such as, for example, filters, wire guides, and cerebral aneurysm filler coils.

Figure 7A:
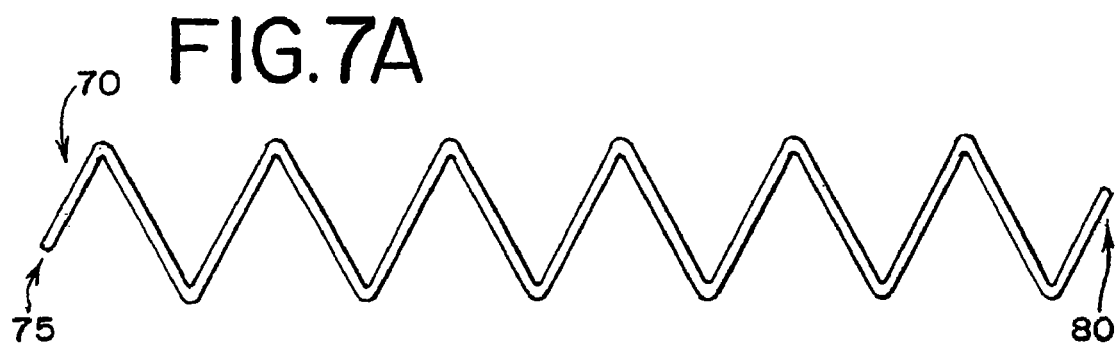
FIG. 7A shows schematically a wire having a zig-zag configuration.
Figure 7B:
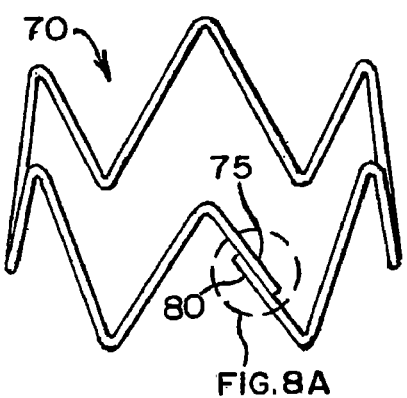
FIG. 7B shows schematically the wire of FIG. 7A configured to form a stent.

In another example, the bonding method may be employed in fabricating a stent, such as a self-expanding stent. The stent may be made from a nickel-titanium alloy wire that is formed in a zig zag pattern, for example, as shown schematically in FIG. 7A, and then curved to form a ring, as shown in FIG. 7B. The bonding method described herein may be advantageously employed to diffusion bond one end of the wire to the other to form the stent.

Figure 8A:
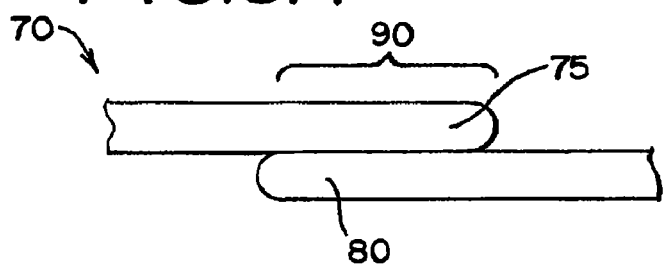
FIG. 8A is a close-up view of ends of the wire of FIGS. 7A and 7B in an assembled configuration for bonding, according to one embodiment.
Figure 8B:
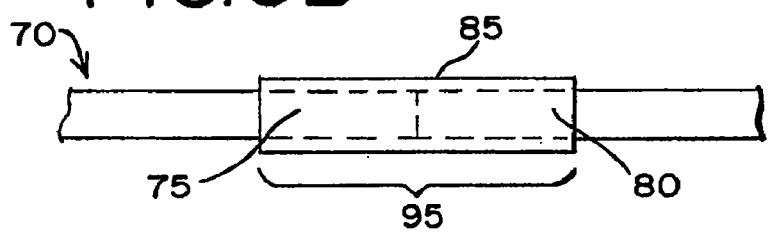
FIG. 8B is a close-up view of ends of the wire of FIG. 7A in an assembled configuration for bonding, according to another embodiment.

Referring to FIGS. 8A and 8B, the first component employed in the bonding method according to this example is a first end 75 of the wire 70, and the second component is a second end 80 of the wire 70. The first and second ends 75, 80 of the wire 70 may be placed alongside one another in an overlapping assembled configuration 90 so as to form a substantial region of contact for bonding, as shown schematically in FIG. 8A. Alternatively, the ends 75, 80 may be placed end-to-end for bonding, in which case a third component (e.g., a cannula 85) is preferably included in the assembled configuration 95 to hold the ends together and increase the region of contact for bonding, as shown schematically in FIG. 8B. A press-fit as described above may be obtained between the cannula 85 and the first and second ends 75, 80 of the wire 70. Like the wire 70, the cannula 85 is desirably formed of a nickel-titanium alloy.

Preferably, during heat treatment of the assembled configuration 90 shown in FIG. 8A, a diffusion bond is formed at a region of contact between the first and second components (i.e., the first and second ends 75, 80). Preferably, during heat treatment of the assembled configuration 95 shown in FIG. 8B, a diffusion bond is formed not only at the region of contact between the first and second ends 75, 80, but also at a region of contact between the first end 75 and the cannula 85 and at a region of contact between the second end 80 and the cannula 85. The heat treatment may be carried out as described previously. After heat treating to form the diffusion bond, the assembled configuration may be formed into a desired set shape and heat-set as described above.

EXAMPLES

Experiments were conducted to join nickel-titanium components by way of solid state diffusion bonding, as described above, and then to heat set the bonded assembly. A tantalum intermediary layer was employed in some tests to enhance bonding. The process may be used, for example, to attach Ni—Ti alloy wire to Ni—Ti alloy cannula for assembly of wire Z-stents for endovascular stent-graft devices.

Materials and Methods

A single spool of Ni—Ti alloy wire (catalog reference NiTi#1-CW) was obtained from Fort Wayne Metals (FWM) for these experiments. The wire had a diameter of 355.5 µm (0.014 inches) and was received from the vendor with a light oxide finish. The continuous spool of Ni—Ti alloy wire from FWM was cut into approximately 50-mm length pieces.

A subset of the wire samples was set aside for Ta sputter coating treatments. A Cressington 308R desktop coater equipped with a 57-mm diameter by 0.011 in thick Ta sputter target guide was used to apply a thin coating of Ta to the Ni—Ti alloy wire specimens. Each wire specimen was coated for 60 seconds before being rotated 90 degrees about a longitudinal axis of the wire and coated for an additional 60 seconds and then rotated another 90 degrees and coated for an additional 60 seconds for a total of 360 degrees and 240 seconds of coating. The entire surface of the wire thus received some amount of Ta.

Two groups of Ni—Ti alloy wire samples, one with a Ta-coated Ni—Ti alloy wire in contact with an uncoated Ni—Ti alloy wire and the other with two uncoated Ni—Ti alloy wires in contact with each other, were carefully arranged between alumina plates and placed in a horizontal vacuum furnace. Wires were positioned one over another in a crossed position to create an overlapped assembled configuration suitable for the bonding tests.

The vacuum furnace underwent a check for leaks to verify the integrity of the apparatus, and a clean-up cycle was completed just prior to the bonding heat treatments.

The Ni—Ti alloy wire samples were raised to a soak temperature of 1000° C. at a rate of 25° C./min and held at the soak temperature under full vacuum for 45 minutes with a constant applied load of approximately 15 N (from the upper alumina plate). During this time, a diffusion bond was formed between the wires at a region of contact in the overlapped assembled configuration. After the soak, the bonded wire specimens were quenched under a partial pressure of argon gas.

Following diffusion bonding, the bonded wire specimens were further processed in a convection oven to simulate typical heat setting conditions for Ni—Ti alloy wire. The wire specimens were placed onto alumina setters in the oven and held at 500° C. for 10 minutes. After heat setting, the wire specimens were removed from the oven and quickly transferred to a beaker of room-temperature tap water to quench.

Results

The bonded area of each sample was analyzed after heat setting using a Hitachi scanning electron microscope (SEM). FIGS. 9A-9B show the tantalum-coated nickel-titanium wire bonded to the uncoated nickel-titanium wire, and FIGS. 10A-10B show the uncoated nickel-titanium wires bonded to each other. The joint between the Ni—Ti alloy wires was found to be slightly weaker than the bond formed between the Ta-coated wire and an uncoated Ni—Ti alloy wire. As the figures show, the bond in each assembled configuration was accompanied by considerable deformation of the wires.

To estimate the austenite finish temperature ($A_f$) of the bonded wire assemblies after the heat setting treatment, bend and free recovery tests were carried out according to the following procedure. The bonded wire assemblies were (1) immersed in liquid nitrogen to cool to a low temperature, (2) deformed to a prescribed strain (e.g., about 2-3%) while immersed in liquid nitrogen, (3) removed from the liquid nitrogen and observed as they warmed up to room temperature. The temperature at which the bonded assemblies returned to their original shape was recorded. This temperature is representative of $A_f$, and was confirmed to be below body temperature (37° C.) by the tests.

The inventors believe the diffusion bonding experiments show that: (1) solid-state diffusion bonding of nickel-titanium alloy components as described above can generate adhesion at a region of contact between the components, and (2) heat setting under conditions suitable for imparting a remembered shape and desired transformation temperature values to the Ni—Ti alloy alloy components may be carried out successfully without impairing the bond between the wires.

A method for diffusion bonding a first component of a medical device to a second component of the medical device that may overcome limitations of previous attachment methods has been described herein. The bonding method allows for the fabrication of a bonded assembly having superelastic properties. Preferably, one or both components of the medical device are formed in whole or in part of a shape memory material.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of bonding one component of a medical device to another component of the medical device, the method comprising:
    positioning a first component in close proximity to a second component to form an assembled configuration, at least one of the first and second components comprising a shape memory material;
    heat treating the assembled configuration at a temperature in the range of from about 800° C. to about 1100° C. to form a diffusion bond between the first component and the second component at a region of contact between the components;
    forming the assembled configuration into a desired set shape; and
    heat setting the assembled configuration at a temperature in the range of from about 350° C. to about 550° C. to impart a memory of the desired set shape to the shape memory material without substantially impairing the diffusion bond between the components,
    wherein the heat treating is carried out for a duration in the range of from about 15 minutes to about 60 minutes and the heat setting is conducted for a duration in the range of from about 10 minutes to about 30 minutes.

2. The method of claim 1, wherein positioning the first component in close proximity to the second component comprises obtaining a press-fit between the first and second components.

3. The method of claim 1, further comprising disposing a third component about the first and second components to form the assembled configuration.

4. The method of claim 1, wherein pressure is applied to the region of contact during the heat treating.

5. The method of claim 4, wherein the pressure has an average value in the range of from about 50 psi to about 500 psi.

6. The method of claim 4, wherein the pressure is an internal pressure generated by a change in dimension of at least one of the first and second components in response to elevated temperature exposure.

7. The method of claim 6, wherein the shape memory material comprises a martensitic phase during the positioning, and wherein warming the assembled configuration to a temperature above an austenite finish temperature of the shape memory material causes the change in dimension of at least one of the first and second components.

8. The method of claim 1, wherein the bond is a solid-state diffusion bond.

9. A method of bonding an anchoring element to a portion of a stent, the method comprising:
  positioning an anchoring element in close proximity to a portion of a stent to form an assembled configuration, wherein at least one of the anchoring element and the portion comprises a shape memory material;
  heat treating the assembled configuration at a temperature in the range of from about 800° C. to about 1100° C. to obtain a bond between the anchoring element and the portion at a region of contact therebetween;
  forming the assembled configuration into a desired set shape; and
  heat setting the assembled configuration at a temperature in the range of from about 350° C. to about 550° C. to impart a memory of the desired set shape to the shape memory material without substantially impairing the bond between the anchoring element and the portion of the stent,
  wherein the heat treating is carried out for a duration in the range of from about 15 minutes to about 60 minutes, and the heat setting is conducted for a duration in the range of from about 10 minutes to about 30 minutes.

10. The method of claim 9, wherein the anchoring element comprises an attachment portion and a barb extending from the attachment portion, the attachment portion comprising a thin-walled sleeve configured to at least partially surround the portion of the stent, and wherein the positioning comprises obtaining a press-fit between the attachment portion and the portion of the stent.

11. The method of claim 9, wherein pressure is applied to the region of contact during the heat treating.

12. The method of claim 9, wherein both of the anchoring element and the portion of the stent comprise a shape memory material.

13. The method of claim 9, further comprising coating tantalum on at least one of the anchoring element and the portion of the stent.

14. A method of bonding ends of a wire to form a medical device, the method comprising:
  positioning a first end of a wire in close proximity to a second end of the wire to form an assembled configuration, wherein the wire comprises a shape memory material;
  heat treating the assembled configuration at a temperature in the range of from about 800° C. to about 1100° C. to obtain a bond between the first end and the second end at a region of contact therebetween;
  forming the assembled configuration into a desired set shape; and
  heat setting the assembled configuration at a temperature in the range of from about 350° C. to about 550° C. to impart a memory of the desired set shape to the shape memory material without substantially impairing the bond between the first end and the second end of the wire,
  wherein the heat treating is carried out for a duration in the range of from about 15 minutes to about 60 minutes, and the heat setting is conducted for a duration in the range of from about 10 minutes to about 30 minutes.

15. The method of claim 14, further comprising disposing a third component about the first and second ends of the wire to form the assembled configuration.

16. The method of claim 14, wherein pressure is applied to the region of contact during the heat treating.

17. A method of bonding an anchoring element to a portion of a stent, the method comprising:
  coating tantalum on at least one of an anchoring element and a portion of a stent;
  positioning the anchoring element in close proximity to the portion of a stent to form an assembled configuration, wherein at least one of the anchoring element and the portion comprises a shape memory material;
  heat treating the assembled configuration at a temperature in the range of from about 800° C. to about 1100° C. to obtain a bond between the anchoring element and the portion at a region of contact therebetween;
  forming the assembled configuration into a desired set shape; and
  heat setting the assembled configuration at a temperature in the range of from about 350° C. to about 550° C. to impart a memory of the desired set shape to the shape memory material without substantially impairing the bond between the anchoring element and the portion of the stent.

* * * * *